(12) United States Patent
Sornes

(10) Patent No.: US 11,510,655 B2
(45) Date of Patent: Nov. 29, 2022

(54) METHODS AND SYSTEMS FOR MOTION CORRECTED WIDE-BAND PULSE INVERSION ULTRASONIC IMAGING

(71) Applicant: GE Precision Healthcare LLC, Wauwatosa, WI (US)

(72) Inventor: Anders R. Sornes, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 584 days.

(21) Appl. No.: 16/566,216

(22) Filed: Sep. 10, 2019

(65) Prior Publication Data
US 2021/0068792 A1 Mar. 11, 2021

(51) Int. Cl.
*A61B 8/14* (2006.01)
*A61B 8/08* (2006.01)
*G01S 15/89* (2006.01)
*G01S 7/52* (2006.01)
*A61B 8/00* (2006.01)

(52) U.S. Cl.
CPC .......... *A61B 8/5215* (2013.01); *A61B 8/0883* (2013.01); *A61B 8/14* (2013.01); *A61B 8/463* (2013.01); *A61B 8/483* (2013.01); *G01S 7/52025* (2013.01); *G01S 15/89* (2013.01)

(58) Field of Classification Search
CPC .......... A61B 8/0883; A61B 8/14; A61B 8/463; A61B 8/466; A61B 8/48; A61B 8/483; A61B 8/486; A61B 8/488; A61B 8/5215; A61B 8/5276; G01S 15/89; G01S 15/8954; G01S 15/8963; G01S 7/52025; G01S 7/52026; G01S 7/52038
See application file for complete search history.

(56) References Cited

U.S. PATENT DOCUMENTS

2009/0005679 A1* 1/2009 Dala-Krishna ........... G06T 7/80
600/437

* cited by examiner

*Primary Examiner* — Mark D Remaly
(74) *Attorney, Agent, or Firm* — McAndrews, Held & Malloy, Ltd.; Jacob Groethe; David Bates

(57) ABSTRACT

Systems and methods are provided for motion corrected wide-band pulse inversion ultrasonic imaging. A first pulse is transmitted, a second pulse is then transmitted after a delay, with the second pulse having different polarity. Echoes of the first pulse and the second pulse are received, using a reception bandwidth that enables capturing at least a portion of a fundamental portion of each pulse. The echoes are processed, and corresponding ultrasound images are generated based on processing. The processing includes determining displacement data between the first pulse echo and the echo of the second pulse for at least one structure in an imaged area; determining one or more displacement corrections based on the displacement data; applying at least one displacement correction to at least one of the first pulse echo and the echo of the second pulse; and combining the first pulse echo and the echo of the second pulse.

20 Claims, 5 Drawing Sheets

METHODS AND SYSTEMS FOR MOTION CORRECTED WIDE-BAND PULSE INVERSION ULTRASONIC IMAGING

FIELD

Aspects of the present disclosure relate to medical imaging. More specifically, certain embodiments relate to methods and systems for motion corrected wide-band pulse inversion ultrasonic imaging.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Ultrasound imaging may pose certain challenges in some use scenarios, however. For example, moving structures may be hard to scan and/or may introduce motion-related artifacts during some ultrasound imaging scans, and conventional solutions, if any existed, for addressing challenges posed by such moving structures may be ineffective, inefficient, and/or costly.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for a motion corrected wide-band pulse inversion ultrasonic imaging, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
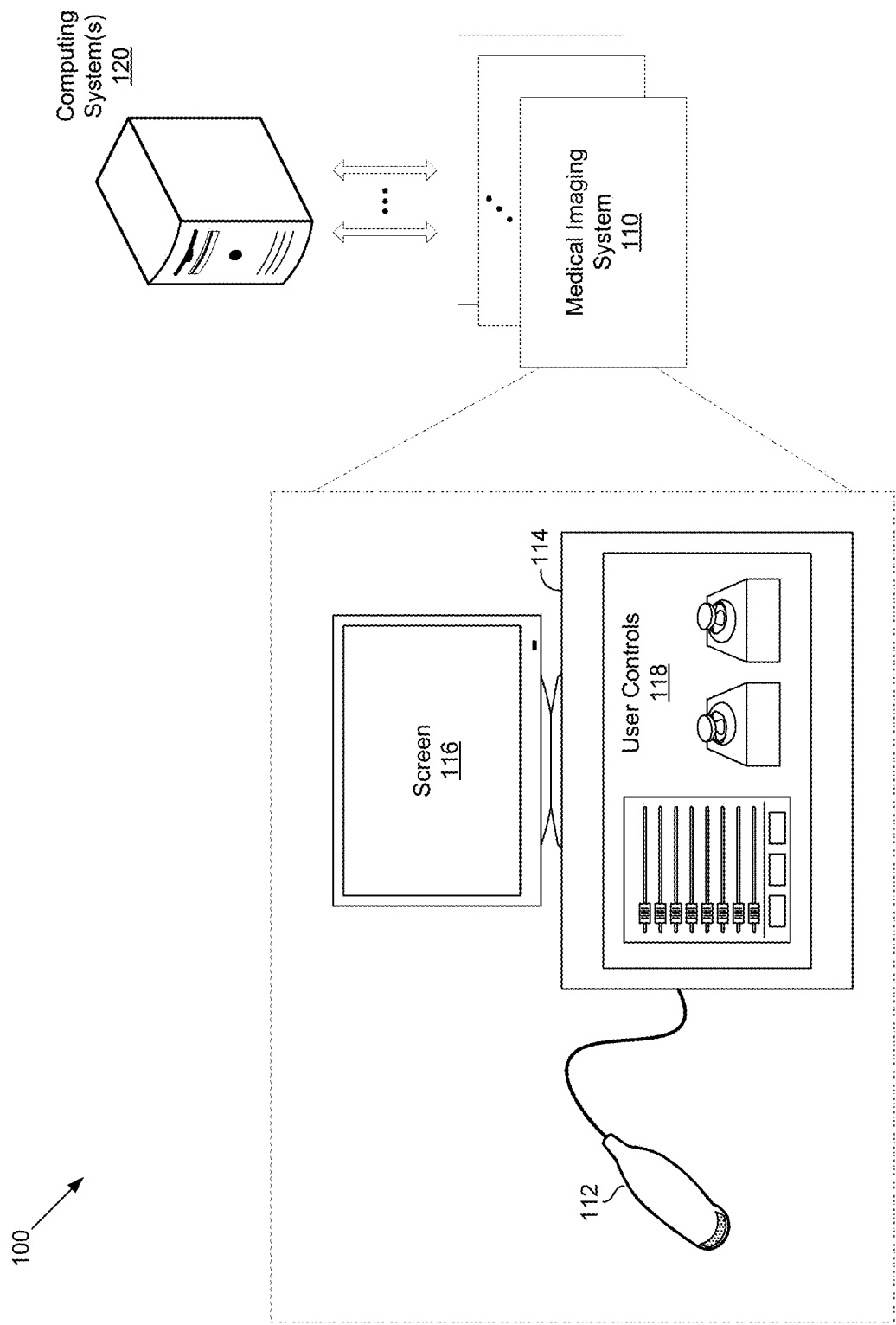
FIG. 1 is a block diagram illustrating an example medical imaging arrangement that supports motion corrected wide-band pulse inversion ultrasonic imaging, in accordance with the present disclosure.

Certain implementations in accordance with the present disclosure may be directed to motion corrected wide-band pulse inversion ultrasonic imaging. In particular, various embodiments have the technical effect of enhancing quality of images, by allowing for detection and/or removal of defects introduced as result of movement in imaged structures (e.g., heart during cardiology imaging). This may be done, for example, by transmitting a first pulse, transmitting a second pulse after a delay, wherein the second pulse has a different polarity relative to the first pulse, receiving echoes of the first and the second pulses, with the reception configured to utilized a bandwidth wide enough to capture at least a portion of a fundamental portion of each pulse, processing the received pulse echoes, with the processing including determining displacement data between the pulse echoes and determining based on the displacement data corresponding motion-related corrections, then applying the motion-related correction to one or both pulse echoes that are subsequently to be combined. Aspects of the present disclosure have the technical effect of allowing for correcting motion-related artifacts that may be introduced by structures moving during multiple ultrasound pulse echo recordings to be combined when imaging areas that include such structures.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIGS. 1 and 2.

Figure 2:
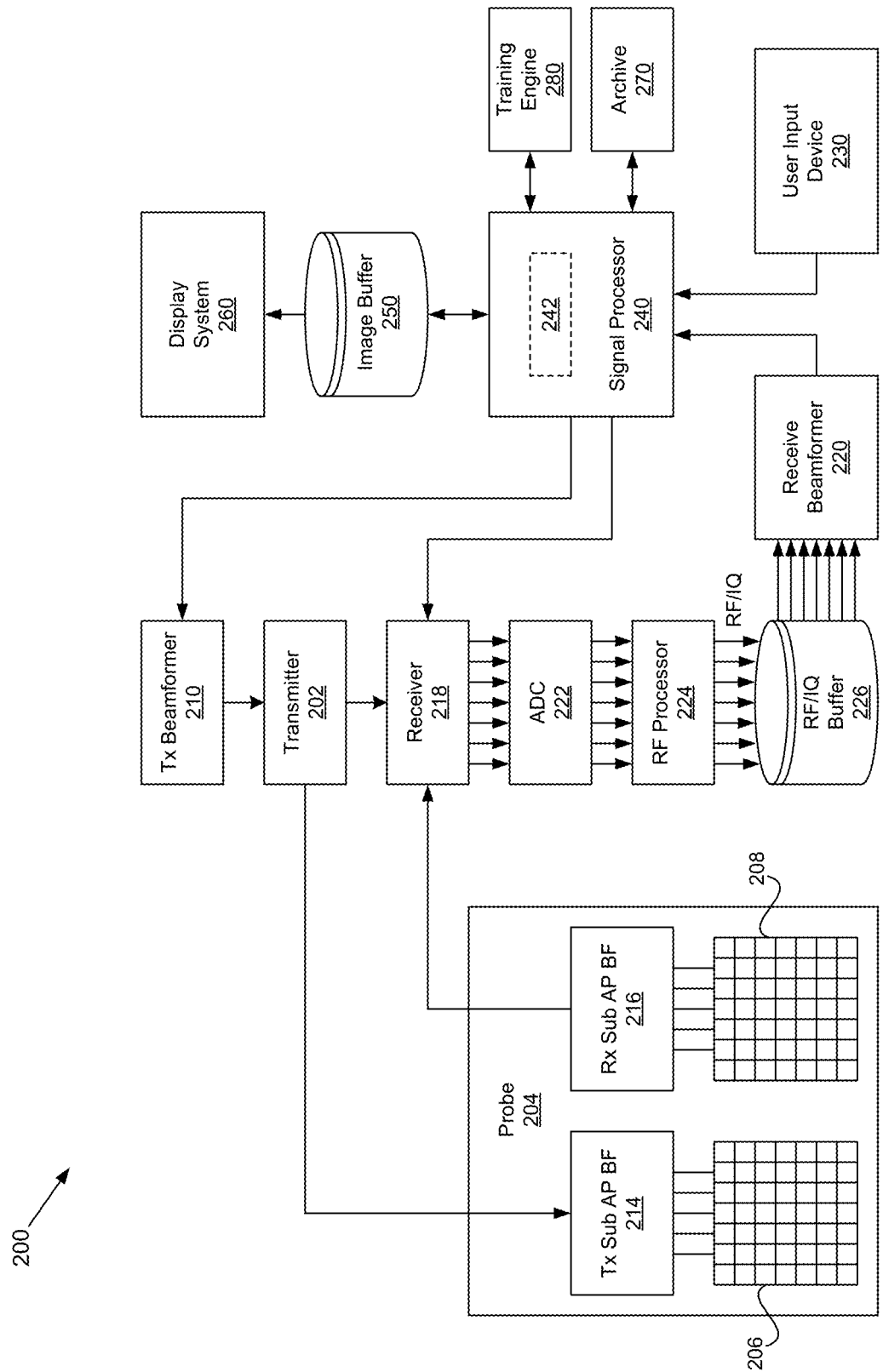
FIG. 2 is a block diagram illustrating an example ultrasound that supports motion corrected wide-band pulse inversion ultrasonic imaging, in accordance with the present disclosure.

FIG. 1 is a block diagram illustrating an example medical imaging arrangement that supports motion corrected wideband pulse inversion ultrasonic imaging, in accordance with the present disclosure. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a probe 112, which may be portable and movable, and a display/control unit 114. The probe 112 may be configured for generating and/or capturing particular type of signals (or data corresponding thereto), such as by being moved over a patient's body (or part thereof). For example, where the medical imaging system 110 is an ultrasound system, the probe 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost (by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other Cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, the medical imaging system 110 may support motion corrected wide-band pulse inversion ultrasonic imaging, as described below.

FIG. 2 is a block diagram illustrating an example ultrasound that supports motion corrected wide-band pulse inversion ultrasonic imaging, in accordance with the present disclosure. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1.

The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270. The user input device 230 may include button(s), rotary encoder(s), a touchscreen, motion tracking, voice recognition, a mouse device, keyboard, camera and/or any other device capable of receiving a user directive. In certain embodiments, one or more of the user input devices 230 may be integrated into other components, such as the display system 260 or the ultrasound probe 204, for example. As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. Additionally and/or alternatively, the user input device 230 may include image analysis processing to identify probe gestures by analyzing acquired image data.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a motion correction module 242, which comprises suitable circuitry, interfaces, logic, and/or code that may be configured to perform and/or support various functions or operations relating to, or in support of motion corrected wide-band pulse inversion ultrasonic imaging, as described in more detail below.

In some implementations, the signal processor 240 (and/or components thereof, such as the motion correction module 242) may be configured to implement and/or use deep learning techniques and/or algorithms, such as using deep neural networks (e.g., a convolutional neural network), and/or may utilize any suitable form of artificial intelligence image analysis techniques or machine learning processing functionality configured to analyze acquired ultrasound images to identify, segment, label, and track structures meeting particular criteria and/or having particular characteristics.

In some implementations, the signal processor 240 (and/or components thereof, such as the motion correction module 242) may be provided as a deep neural network that may be made up of, for example, an input layer, an output layer, and one or more hidden layers in between the input and output layers. Each of the layers may be made up of a plurality of processing nodes that may be referred to as neurons.

For example, the deep neural network may include an input layer having a neuron for each pixel or a group of pixels from a scan plane of an anatomical structure. The output layer may have a neuron corresponding to a plurality of pre-defined structures or types of structures. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the deep neural network (e.g., convolutional neural network) may identify biological and/or artificial structures in ultrasound image data with a high degree of probability.

In certain implementations, the signal processor 240 (and/or components thereof, such as the module 242) may be configured to perform or otherwise control at least some of the functions performed thereby based on a user instruction via the user input device 230. As an example, a user may provide a voice command, probe gesture, button depression, or the like to issue a particular instruction, such as to request performing or applying motion correction, to specific using corrected wide-band pulse inversion (as described below), and/or to provide or otherwise specify various parameters or settings pertinent to performing such motion corrections.

The training engine 280 may comprise suitable circuitry, interfaces, logic, and/or code that may be operable to train the neurons of the deep neural network(s) of the signal processor 240 (and/or components thereof, such as the motion correction module 242). For example, the signal processor 240 may be trained to identify particular structures or types of structures provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the motion correction module 242) with respect to the characteristics of the particular structure(s), such as the appearance of structure edges, the appearance of structure shapes based on the edges, the positions of the shapes relative to landmarks in the ultrasound image data, and the like. In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support motion corrected wide-band pulse inversion ultrasonic imaging. In many instances, ultrasound imaging is carried out with harmonic imaging, particularly with respect to certain types of examination—e.g., in adult cardiology but also in radiology applications. This may make ultrasound imaging susceptible to noise related defects. In this regard, a typical source of noise in ultrasound imaging is reverberation noise. For example, in adult cardiology trans-thoracic scanning views may be interfered with by reverberations from lung and ribs, which may cause noise defects—e.g., covering the moving heart image with haze.

Conventional solutions for removing reverberations, if any existed, may be based on filtering the spectrum and imaging only data formed from the subsequently generated (e.g., second) harmonic components of the spectrum. Such approach may be successful because the reverberations typically propagate more shallowly, and thus may generate less harmonic content than the signal(s) that echoed off the deeper target. The radial resolution of the image may be determined by the bandwidth of the received echoes. However, such filtering may limit the resolution obtained. Moreover, the filter setup needed to suppress the reverberations may differ from subject to subject and may not always be sufficient to remove all haze on difficult to scan patients.

Thus, a different technique may be used to overcome these issues. In particular, in many instances, pulse inversion is utilized. With pulse inversion, two successive pulses are transmitted in each direction comprising the scan, each with a pulse of different (e.g., opposite) polarity. This may be done because the fundamental echo is linear with respect to pulse amplitude, while the second harmonic pulse is quadratic with respect to pulse amplitude. Hence, the addition of the pulses of opposite polarity may lead to a cancelling of the fundamental spectrum component, while enhancing the second harmonic content. Use of such scheme allows the use of large bandwidths both upon transmit and reception because the fundamental contents will be removed by the summation process.

This is however only the case if the imaged object is stationary. If imaged object is moving (e.g., the heart in cardiology imaging), the echo from the same structure will be shifted in time and the summation process will not be able to cancel out the fundamental component of the spectrum. In this regard, the harmonic part of the spectrum is much smaller than the fundamental component so whenever and wherever there are moving parts in the image, a very strong fundamental signal will leak through and light up like a flickering flash in the image.

Thus, implementations in accordance with the present disclosure provide solutions for overcoming such issues, particularly by incorporating measures for compensates for such motion artifacts. This may be done, for example, by estimating the phase difference between the successive pulses, such as by correlation, and averaging the results. If the filter setting is sufficiently wide to encompass a significant component of fundamental energy to dominate the amplitude of the second harmonic component, the phase difference calculated from the correlation of the two pulses will be sufficient to cancel the motion artifacts.

In various example implementations, broad band pulses are used, with each transmitted band pulses being followed by a pulse of opposite polarity. Received echoes from both pulses are then filtered with broad band receive filters. In particular, the broad band filter is configured such that it extends far into the fundamental part of the spectrum, thus ensuring that each pulse alone is dominated by its fundamental frequency contents from the backscattering signal. The correlation between the signal from the first pulse and the negative of the first pulse is then calculated in the entire image. The result may be filtered by a median filter in the radial direction over a period of multiple samples, to generate phase estimation. Alternatively, other suitable filters averaging out fluctuations may be employed. This may be done to utilize the fact that the rigid body may have connected movements in regions of proximity. The resultant phase estimation describes the radial displacements occurring from tissue movements between the two pulses and is applied as a phase rotation of half size and opposite sign to each of the two received IQ signals before these are summed together.

Thus, implementations in accordance with the present disclosure utilize wide reception bandwidths to better detect spatial displacement in the scanned area. In particular, where the receive bandwidth is sufficiently large to go into the fundamental band of the pulse, the spectrum will be dominated by the fundamental contents, and the displacement of the second pulse with respect to the first can be estimated by a correlation calculation between the first pulse and the negated second pulse. Each pulse is then corrected—e.g., with the opposite of half of the phase rotation, which may allow for cancellation of fundamental contents even in the presence of severe tissue motion. As a result, broader bandwidths may be applied in imaging rapid moving tissue (e.g., during cardiac imaging), thus resulting in improving the radial resolution in these kind of recordings significantly.

In an example use case, using a suitable ultrasound system (e.g., ultrasound system 200) configured for supporting motion corrected wide-band pulse inversion ultrasonic imaging, a radio frequency (RF) signal from a single pulse may hit a single scatterer that is moving with constant velocity towards the probe. Assuming that $\delta$ represents the time difference between the orientation of the scatterer at a particular depth position when the first and the second pulse passes, the RF signal may take the following form for the first pulse a(t) and second pulse b(t):

$$a(t) = -p_0(t-\delta/2)\cos(\omega t - \omega\delta/2) + p_2(t-\delta/2)\cos(2\omega t - \omega\delta)$$

$$b(t) = p_0(t+\delta/2)\cos(\omega t + \omega\delta/2) + p_2(t+\delta/2)\cos(2\omega t + \omega\delta)$$

Where $\omega$ is carrier frequency, $p_0$ is the fundamental pressure envelope function, and $p_2$ is the second harmonic is $p_2$.

The envelope function may vary in a much slower rate than the carrier wave, and as such may be considered approximately stationary for the time scale of the shift $\delta$ between pulses:

$$a(t) \approx -p_0 \cos(\omega t - \omega\delta/2) + p_2 \cos(2\omega t - \omega\delta)$$

$$b(t) \approx p_0 \cos(\omega t + \omega\delta/2) + p_2 \cos(2\omega t + \omega\delta)$$

The demodulation of these RF channel data at a frequency $\Omega$, and subsequent filtering of the data, may single out only frequencies close to zero. This may leave only one of the two frequency components of the cosine functions being closest to $\Omega$:

$$A(t) \approx -p_0 e^{j(\omega-\Omega)t} e^{-j\omega\delta/2} + p_2 e^{j(2\omega-\Omega)t} e^{-j\omega\delta}$$

$$B(t) \approx p_0 e^{j(\omega-\Omega)t} e^{j\omega\delta/2} + p_2 e^{j(2\omega-\Omega)t} e^{j\omega\delta}$$

Clearly the harmonic content $p_2$ cannot be obtained by summing the pulses, as the pulse sum will contain fundamental contents which will introduce defects (e.g., contaminating the image with pulsating flashes). Instead, correlation between the two pulses may be used:

$$A^*(t)B(t) = -p_0^2 e^{j\omega\delta} + p_2^2 e^{j2\omega\delta} - p_0 p_2 e^{j\omega t} e^{j\omega 3\delta/2} + p_0 p_2 e^{-j\omega t} e^{j\omega 3\delta/2}$$

$$A^*(t)B(t) = -p_0^2 e^{j\omega\delta} + p_2^2 e^{j2\omega\delta} - 2jp_0 p_2 \sin \omega t\, e^{j\omega 3\delta/2}$$

In this regard, the expression for the correlation is independent of the mixing frequency $\Omega$. The phase correction term caused by the motion is $e^{j\omega\delta}$. Since the motion is set up by a rigid body, the target motion may change on a much lower scale than the frequency $\omega$, and hence the expression for the correlation may be averaged over one cycle, thus nulling the only time dependent term, which gives:

$$-p_0^2 e^{j\omega\delta} + p_2^2 e^{j2\omega\delta} = \frac{\omega}{2\pi} \int_{-\pi/\omega}^{+\pi/\omega} A^*(t)B(t)dt$$

Since $p_0 \gg p_2$ under the assumption that the filtering has been carried out preserving a significant amount of fundamental spectral component we can approximate this to:

$$e^{j\omega\delta} = \frac{-\frac{\omega}{2\pi}\int_{-\pi/\omega}^{+\pi/\omega} A^*(t)B(t)dt}{\left|\frac{\omega}{2\pi}\int_{-\pi/\omega}^{+\pi/\omega} A^*(t)B(t)dt\right|}$$

This correction may now be applied to the original data to ensure fundamental component cancellation by:

$$A(t)e^{j\omega\delta/2} + B(t)e^{-j\omega\delta/2} = p_2 e^{j(2\omega-\Omega)t} 2\cos\left(\frac{\omega\delta}{2}\right)$$

Thus, pre-multiplying the positive and negative pulse in the pulse inversion sequence may allow subsequent pulse summation to remove the fundamental component of the signal in the vicinity of tissue motion—that is, if the correlation estimate between the two pulses are averaged over a small radial region and the bandwidth of the received echo is sufficiently large to ensure a dominating component of fundamental signal in each component pulse.

These calculations and/or determinations made based thereon may be performed in the motion correction module 242, for example. In some implementations, correlation between the pulses may also be estimated on channel data prior to beamforming. This may be done by picking only one central channel of data to estimate from, or may be averaged over all the channels. If this is done without delay compensating, the resultant field may be smoothed.

Figure 3:
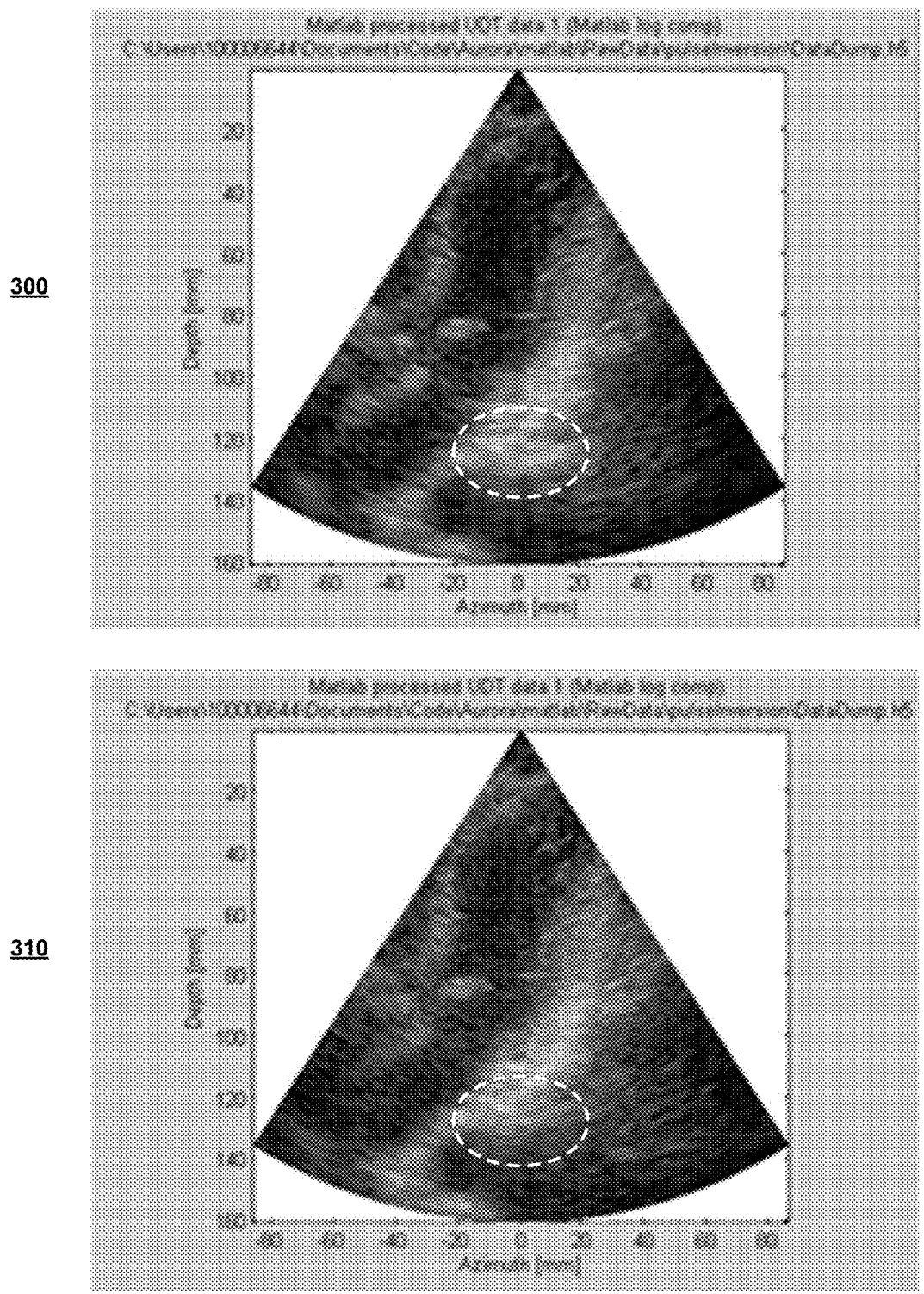
FIG. 3 illustrates example ultrasound images generated with and without wide-band pulse inversion based motion corrections, in accordance with various embodiments.

FIG. 3 illustrates example ultrasound images generated with and without wide-band pulse inversion based motion corrections, in accordance with various embodiments. Shown in FIG. 3 are screenshots of ultrasound images generated during ultrasound imaging scan of an area with moving structures.

In particular, screenshot 300 illustrates an ultrasound image generated without motion-correction. In this regard, image 300 is generated using broad and low frequency band filtered ultrasound data from pulse inversion without any compensation. As illustrated in FIG. 3, image 300 exhibits motion-related artifacts (e.g., within area of the image circled with a dash closed line), corresponding to scanned areas that are dominated by very high fundamental contents, caused by failure to cancel the opposite polarity pulses due to motion. The areas vary through the cycle and give a "pumping" look during active (but in a still frame, as shown in FIG. 3, these areas appear as smearing out and blooming).

Screenshot 310 illustrates an ultrasound image generated with wide-band pulse inversion based motion corrections, in accordance with the present disclosure—e.g., based on use of phase adjustments calculated in the manner described with respect to FIG. 2. In this regard, as result of applying the motion compensation adjustments, based on the correlation calculations, the motion-corrected image 310 exhibits more restrained depiction of moving structures (e.g., wall within the heart) with little blooming and smearing outside the expected region. As a result, the motion-corrected image 310 does not "pump" but rather has stable gain, which eliminates or reduces the motion-related artifacts that otherwise would have been created—e.g., as illustrated in the same area as the one circled in image 300.

Figure 4:
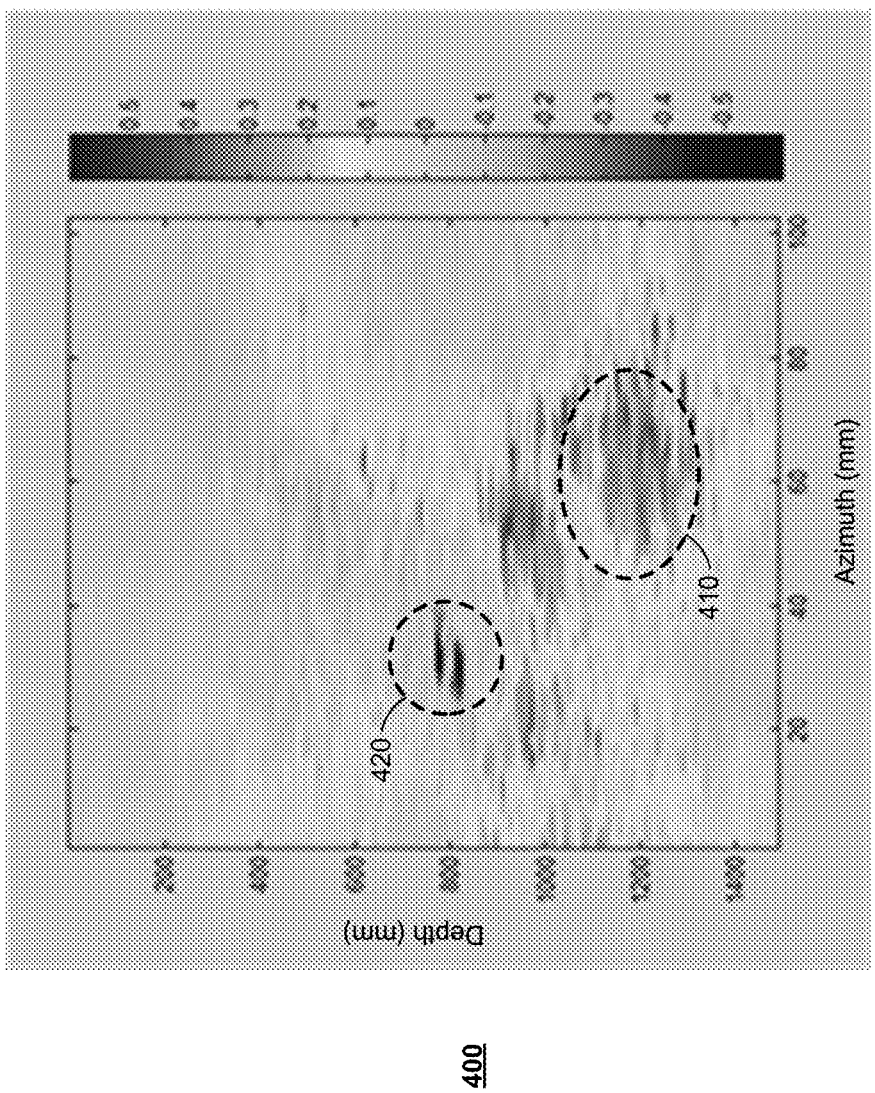
FIG. 4 illustrates an example displacement field calculated based on use of two pulses in an ultrasound image, in accordance with various embodiments.

FIG. 4 illustrates an example displacement field calculated based on use of two pulses in an ultrasound image, in accordance with various embodiments. Shown in FIG. 4 is a chart 400.

The chart 400 illustrates a displacement field that may be generated based on correlation calculation between first pulse(s) and corresponding negated second pulse(s). In this regard, the displacement field 400 as shown in FIG. 4 is generated based on the two pulses corresponding to the image(s) in FIG. 3 (but without scan conversion, thus with the geometry being distorted in the near field).

The displacement field 400 is generated based on correlation calculations between first pulse and second negated pulse for the entire image. The correlation calculations may be used in generating phase estimations, such as based on median filtering in the radial direction—e.g., median filtered by 3 taps in each direction. The resultant phase estimations may describe the radial displacements occurring from tissue movements between the two pulses, such as within area 410 in chart 400. Thus allowing for identifying areas affected by movement—that is areas where the two pulse indicates movement in different directions, such as in area 420 as shown in chart 400.

Figure 5:
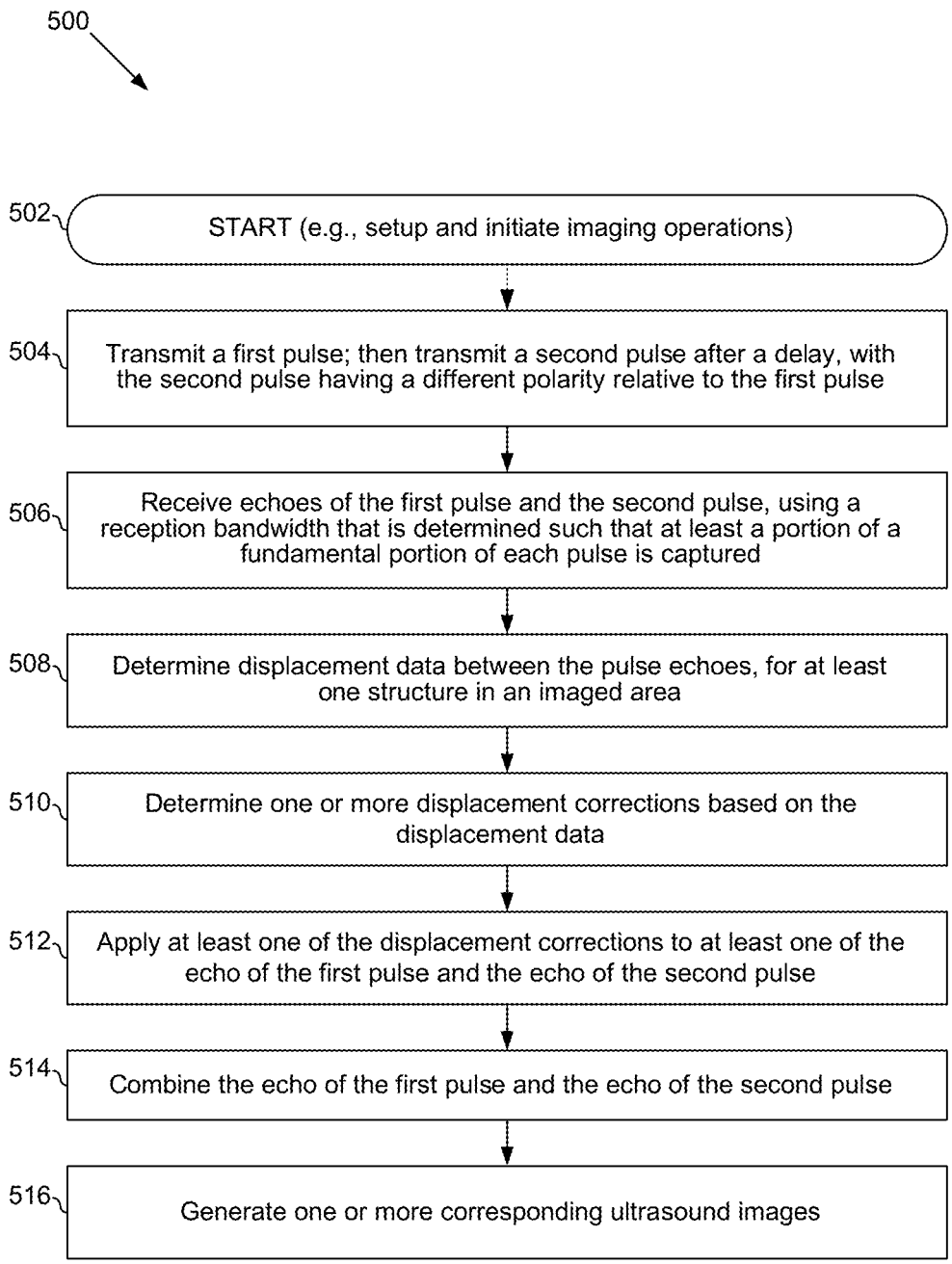
FIG. 5 illustrates a flowchart of an example steps that may be performed for ultrasound imaging with motion corrected wide-band pulse inversion ultrasonic imaging.

FIG. 5 illustrates a flowchart of an example steps that may be performed for ultrasound imaging with motion corrected wide-band pulse inversion ultrasonic imaging.

Shown in FIG. 5 is flow chart 500, comprising a plurality of example steps (represented as blocks 502-516), which may be performed in a suitable system (e.g., system 200 of FIG. 2) for performing motion corrected wide-band pulse inversion ultrasonic imaging.

In start step 502, the system may be setup, and operations may initiate.

In step 504, a first pulse is transmitted; then a second pulse is transmitted after a delay, with the second pulse having a different (e.g., opposite) polarity relative to the first pulse.

In step 506, Receive echoes of the first pulse and the second pulse, using a reception bandwidth that is determined such that at least a portion of a fundamental portion of each pulse is captured.

In step 508, displacement data between the pulse echoes may be determined. In this regard, the displacement data may correspond to at least one structure in an imaged area. The determining of displacement data may comprise determining phase difference between the two pulse echoes.

In step 510, one or more displacement corrections may be determined based on the displacement data.

In step 512, at least one of the displacement corrections may be applied to at least one of the echo of the first pulse and the echo of the second pulse.

In step 514, the echo of the first pulse and the echo of the second pulse may be combined (e.g., summed).

In step 516, one or more corresponding ultrasound images may be generated, based on the combined echoes (including applied correction), and then displayed.

An example method for ultrasound imaging in accordance with the present disclosure comprises transmitting a first pulse; transmitting a second pulse after a delay, with the second pulse having a different polarity relative to the first pulse; receiving echo of the first pulse and echo of the second pulse, with the receiving configured for using a reception bandwidth that is determined such that at least a portion of a fundamental portion of each pulse is captured; processing the echo of the first pulse and the echo of the second pulse; generating based on processing of the echo of the first pulse and the echo of the second pulse, one or more corresponding ultrasound images; and displaying the one or more ultrasound images. The processing comprises determining displacement data between the echo of the first pulse and the echo of the second pulse for at least one structure in an imaged area; determining one or more displacement corrections based on the displacement data; applying at least one of the one or more displacement corrections to at least one of the echo of the first pulse and the echo of the second pulse; and combining the echo of the first pulse and the echo of the second pulse;

In an example implementation, the second pulse has opposite polarity relative to the first pulse.

In an example implementation, the method further comprises determining displacement data between the echo of the first pulse and the echo of the second pulse for each pixel in corresponding ultrasound image.

In an example implementation, the method further comprises configuring at least one of the one or more displacement corrections based on motion of the at least one structure and/or reflections of surrounding tissues.

In an example implementation, the method further comprises splitting the one or more displacement corrections into a first subset and a second subset; applying one of the first subset and a second subset to one of the echo of the first pulse and the echo of the second pulse; and applying other one of the first subset and a second subset to other one of the echo of the first pulse and the echo of the second pulse.

In an example implementation, the method further comprises applying at least one of the one or more displacement corrections to both of the echo of the first pulse and the echo of the second pulse.

In an example implementation, the method further comprises applying each of the one or more displacement corrections to both of the echo of the first pulse and the echo of the second pulse.

In an example implementation, determining the displacement data comprises determining estimates for phase difference between the echo of the first pulse and the echo of the second pulse; and determining at least part of the displacement data based on the phase difference estimate.

In an example implementation, the method further comprises determining at least one smoothing correction to at least one surrounding area in proximity of the at least one structure; and applying the at least one smoothing correction during the processing of the echo of the first pulse and the echo of the second pulse, one or more corresponding ultrasound images, the generating of the one or more corresponding ultrasound images, and the displaying of the one or more ultrasound images.

An example system for ultrasound imaging in accordance with the present disclosure comprises a transceiver and one or more circuits, with the transceiver configured to transmit a first pulse; transmit a second pulse after a delay, wherein the second pulse has a different polarity relative to the first pulse; and receive echo of the first pulse and echo of the second pulse, wherein the receiving is configured for using a reception bandwidth that is determined such that at least a portion of a fundamental portion of each pulse is captured; and the one or more circuits are configured to process the echo of the first pulse and the echo of the second pulse. The processing comprises determining displacement data between the echo of the first pulse and the echo of the second pulse for at least one structure in an imaged area; determining one or more displacement corrections based on the displacement data; applying at least one of the one or more displacement corrections to at least one of the echo of the first pulse and the echo of the second pulse; and combining the echo of the first pulse and the echo of the second pulse.

In an example implementation, the system configures the second pulse to have opposite polarity relative to the first pulse.

In an example implementation, the one or more circuits are configured to determine displacement data between the echo of the first pulse and the echo of the second pulse for each pixel in a corresponding ultrasound image.

In an example implementation, the one or more circuits are configured to set or adjust at least one of the one or more displacement corrections based on motion of the at least one structure and/or reflections of surrounding tissues.

In an example implementation, the one or more circuits are configured to split the one or more displacement corrections into a first subset and a second subset; apply one of the first subset and a second subset to one of the echo of the first pulse and the echo of the second pulse; and apply other one of the first subset and a second subset to other one of the echo of the first pulse and the echo of the second pulse.

In an example implementation, the one or more circuits are configured to apply at least one of the one or more displacement corrections to both of the echo of the first pulse and the echo of the second pulse.

In an example implementation, the one or more circuits are configured to apply each of the one or more displacement corrections to both of the echo of the first pulse and the echo of the second pulse.

In an example implementation, the one or more circuits are configured to determine estimates for phase difference between the echo of the first pulse and the echo of the second pulse; and determine at least part of the displacement data based on the phase difference estimate.

In an example implementation, the one or more circuits are configured to determine at least one smoothing correction to at least one surrounding area in proximity of the at least one structure.

In an example implementation, the one or more circuits are configured to generate based on processing of the echo of the first pulse and the echo of the second pulse, one or more corresponding ultrasound images.

In an example implementation, the system further comprises a display configured for displaying the one or more ultrasound images.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for ultrasound imaging, the method comprising:
   transmitting a first pulse;
   transmitting a second pulse after a delay, wherein the second pulse has a different polarity relative to the first pulse;
   receiving echo of the first pulse and echo of the second pulse, wherein the receiving is configured for using a reception bandwidth that is determined such that at least a portion of a fundamental portion of each pulse is captured;
   processing the echo of the first pulse and the echo of the second pulse, wherein the processing comprises:
      determining displacement data between the echo of the first pulse and the echo of the second pulse for at least one structure in an imaged area;
      determining one or more displacement corrections based on the displacement data;
      applying at least one of the one or more displacement corrections to at least one of the echo of the first pulse and the echo of the second pulse; and
      combining the echo of the first pulse and the echo of the second pulse;
   generating based on processing of the echo of the first pulse and the echo of the second pulse, one or more corresponding ultrasound images; and
   displaying the one or more ultrasound images.

2. The method of claim 1, wherein the second pulse has opposite polarity relative to the first pulse.

3. The method of claim 1, comprising determining displacement data between the echo of the first pulse and the echo of the second pulse for each pixel in corresponding ultrasound image.

4. The method of claim 1, comprising configuring at least one of the one or more displacement corrections based on motion of the at least one structure and/or reflections of surrounding tissues.

5. The method of claim 1, comprising:
   splitting the one or more displacement corrections into a first subset and a second subset;
   applying one of the first subset and a second subset to one of the echo of the first pulse and the echo of the second pulse; and
   applying other one of the first subset and a second subset to other one of the echo of the first pulse and the echo of the second pulse.

6. The method of claim 1, comprising applying at least one of the one or more displacement corrections to both of the echo of the first pulse and the echo of the second pulse.

7. The method of claim 1, comprising applying each of the one or more displacement corrections to both of the echo of the first pulse and the echo of the second pulse.

8. The method of claim 1, wherein determining the displacement data comprises:
   determining estimates for phase difference between the echo of the first pulse and the echo of the second pulse; and
   determining at least part of the displacement data based on the phase difference estimate.

9. The method of claim 1, comprising:
   determining at least one smoothing correction to at least one surrounding area in proximity of the at least one structure; and
   applying the at least one smoothing correction during:
      the processing of the echo of the first pulse and the echo of the second pulse, one or more corresponding ultrasound images;
      the generating of the one or more corresponding ultrasound images; and
      the displaying of the one or more ultrasound images.

10. A system for ultrasound imaging, the system comprising:
    a transceiver configured to:
       transmit a first pulse;
       transmit a second pulse after a delay, wherein the second pulse has a different polarity relative to the first pulse; and
       receive echo of the first pulse and echo of the second pulse, wherein the receiving is configured for using a reception bandwidth that is determined such that at least a portion of a fundamental portion of each pulse is captured; and
    circuitry configured to process the echo of the first pulse and the echo of the second pulse, wherein the processing comprises:
       determining displacement data between the echo of the first pulse and the echo of the second pulse for at least one structure in an imaged area;
       determining one or more displacement corrections based on the displacement data;
       applying at least one of the one or more displacement corrections to at least one of the echo of the first pulse and the echo of the second pulse; and
       combining the echo of the first pulse and the echo of the second pulse.

11. The system of claim 10, wherein the circuitry is configured to configure the second pulse to have opposite polarity relative to the first pulse.

12. The system of claim 10, wherein the circuitry is configured to determine displacement data between the echo of the first pulse and the echo of the second pulse for each pixel in a corresponding ultrasound image.

13. The system of claim 10, wherein the circuitry is configured to set or adjust at least one of the one or more displacement corrections based on motion of the at least one structure and/or reflections of surrounding tissues.

14. The system of claim 10, wherein the circuitry is configured to:
    split the one or more displacement corrections into a first subset and a second subset;
    apply one of the first subset and a second subset to one of the echo of the first pulse and the echo of the second pulse; and
    apply other one of the first subset and a second subset to other one of the echo of the first pulse and the echo of the second pulse.

15. The system of claim 10, wherein the circuitry is configured to apply at least one of the one or more displacement corrections to both of the echo of the first pulse and the echo of the second pulse.

16. The system of claim 10, wherein the circuitry is configured to apply each of the one or more displacement corrections to both of the echo of the first pulse and the echo of the second pulse.

17. The system of claim 10, wherein the circuitry is configured to:
   determine estimates for phase difference between the echo of the first pulse and the echo of the second pulse; and
   determine at least part of the displacement data based on the phase difference estimate.

18. The system of claim 10, wherein the circuitry is configured to determine at least one smoothing correction to at least one surrounding area in proximity of the at least one structure.

19. The system of claim 10, wherein the circuitry is configured to generate based on processing of the echo of the first pulse and the echo of the second pulse, one or more corresponding ultrasound images.

20. The system of claim 19, further a display configured for displaying the one or more ultrasound images.

* * * * *